US005578079A

United States Patent [19]

Kamel et al.

[11] Patent Number: 5,578,079
[45] Date of Patent: Nov. 26, 1996

[54] BIOCOMPATIBLE, SURFACE MODIFIED MATERIALS

[75] Inventors: Ihab Kamel, Drexel Hill; David B. Soll, Rydal, both of Pa.

[73] Assignees: Drexel University; Ophthalmic Research Corporation, both of Philadelphia, Pa.

[21] Appl. No.: 48,036

[22] Filed: Apr. 14, 1993

Related U.S. Application Data

[60] Division of Ser. No. 820,169, Jan. 13, 1992, Pat. No. 5,260,093, which is a continuation-in-part of Ser. No. 342,270, Apr. 24, 1989, Pat. No. 5,080,924.

[51] Int. Cl.[6] .................................................. A61F 2/16
[52] U.S. Cl. ........................... 623/6; 623/11; 623/66; 427/2.24; 427/2.25; 351/160 R
[58] Field of Search ........................ 623/6, 1, 11, 66; 427/2.24, 2.25, 412.1, 412.2, 412.3, 412.4, 412.5; 351/160 R

[56] References Cited

U.S. PATENT DOCUMENTS

| | | | |
|---|---|---|---|
| 2,999,056 | 9/1961 | Tanner | 522/118 |
| 3,228,741 | 1/1966 | Becker | 351/160 R |
| 3,880,818 | 4/1975 | Shen et al. | 526/322 |
| 3,925,178 | 12/1975 | Gesser et al. | 204/165 |
| 3,944,709 | 3/1976 | Levy | 428/409 |
| 3,959,105 | 5/1976 | Feneberg et al. | 204/165 |
| 3,961,379 | 6/1976 | Highgate | 522/116 |
| 3,985,697 | 10/1976 | Urbach | 523/106 |
| 4,055,378 | 10/1977 | Feneberg et al. | 351/160 |
| 4,072,769 | 2/1978 | Lidel | 427/38 |
| 4,096,315 | 6/1978 | Kubacki | 428/412 |
| 4,099,859 | 7/1978 | Merrill | 351/160 H |
| 4,122,942 | 10/1978 | Wolfson | 206/5.1 |
| 4,123,308 | 10/1978 | Nowlin et al. | 427/41 |
| 4,131,691 | 12/1978 | Morley et al. | 427/41 |
| 4,137,365 | 1/1979 | Wydeven et al. | 428/412 |
| 4,143,949 | 3/1979 | Chen | 427/41 |
| 4,189,364 | 2/1980 | Aelion et al. | 522/4 |
| 4,214,014 | 7/1980 | Hofer et al. | 427/40 |
| 4,240,163 | 12/1980 | Galin | 623/6 |
| 4,277,595 | 7/1981 | Deichert et al. | 528/26 |
| 4,311,828 | 1/1982 | Imada et al. | 528/483 |
| 4,312,575 | 1/1982 | Peyman et al. | 351/160 H |
| 4,328,257 | 5/1982 | Muehlberger et al. | 427/34 |
| 4,344,981 | 8/1982 | Imada et al. | 427/40 |
| 4,405,773 | 9/1983 | Loshaek et al. | 526/318.42 |
| 4,409,258 | 10/1983 | Feurer et al. | 427/38 |
| 4,430,458 | 2/1984 | Tighe et al. | 523/108 |
| 4,463,148 | 7/1984 | Hofer et al. | 526/264 |
| 4,478,873 | 10/1984 | Masso et al. | 427/40 |
| 4,560,458 | 12/1985 | Ueno et al. | 204/165 |
| 4,632,842 | 12/1986 | Karwoski et al. | 427/2 |
| 4,656,083 | 4/1987 | Hoffman et al. | 427/41 |
| 4,718,907 | 1/1988 | Karwoski et al. | 623/12 |
| 4,720,512 | 1/1988 | Hu et al. | 523/112 |
| 4,731,079 | 3/1988 | Stoy | 623/6 |
| 4,731,080 | 3/1988 | Galin | 623/6 |
| 4,806,382 | 2/1989 | Goldberg et al. | 623/6 X |
| 4,836,884 | 6/1989 | McAuslan | 427/2.24 X |
| 4,851,003 | 7/1989 | Lindstrom | 427/2.24 X |
| 4,851,009 | 7/1989 | Pinchue | 427/2.25 X |
| 4,865,870 | 9/1989 | Hu et al. | 427/2 |
| 4,885,077 | 12/1989 | Karakelle et al. | 427/41 |
| 4,919,659 | 4/1990 | Horbett et al. | 427/2 |
| 4,927,676 | 5/1990 | Williams et al. | 427/2 |
| 4,959,074 | 9/1990 | Halpern et al. | 623/6 X |
| 4,979,959 | 12/1990 | Guire | 623/6 X |
| 5,002,582 | 3/1991 | Guire et al. | 623/66 |
| 5,091,204 | 2/1992 | Ratner et al. | 427/2 |
| 5,171,267 | 12/1992 | Ratner et al. | 623/6 |
| 5,252,628 | 10/1993 | Chirila et al. | 623/6 X |

FOREIGN PATENT DOCUMENTS 2119957  11/1983  United Kingdom ............... 351/160 R

OTHER PUBLICATIONS

H. Yasuda, "Plasma for Modification of Polymers", *J. Macromol. Sci.-Chem.*, A10(3), pp. 383–420 (1976).

Knight et al., "Surface Modification of Intraocular Lenses to Reduce Corneal Endothelial Damage", *AM Intra-Ocular Implant Soc.* J–vol. V, pp. 123–130, Apr. 1979.

Gazard et al., "Lithographic Technique Using Radiation-Induced Grafting of Acrylic Acid into Poly (–Methyl Methacrylate) Films", *Polymer Engineering and Science*, vol. 20, No. 16, pp. 1069–1072 (1980).

K. L. Mittal, "Interfacial Chemistry and Adhesion: Recent Developments and Prospects", *Pure & Appl. Chem.*, vol. 52, pp. 1295–1305 (1980).

Akovali et al., "Polymerization of Hexamethyldisiloxane by Plasma on Activated Charcal: Investigation of Parameters", *Journal of Applied Polymer Science*, vol. 29, pp. 2617–2625 (1984).

Lui et al., "Polymethyl Methacrylate Resist Sensitivity Enhancement in X-Ray Lithography by In Situ Polymerization", *Appl. Phys. Lett.*, 44(10), pp. 973–975, May 15, 1984.

Keates et al., "Coated Intraocular Lenses", *Ophthalmic Surgery*, vol. 18, No. 9, pp. 693–697 (1987).

*Primary Examiner*—David J. Isabella
*Attorney, Agent, or Firm*—Panitch Schwarze Jacobs & Nadel, P.C.

[57] ABSTRACT

A method of permanently modifying the surface of a substrate material so as to develop a microscopically smooth, biocompatible surface thereon comprises covalently grafting a biocompatible polymeric material to the surface of the substrate material by radio frequency plasma-induced grafting. The biocompatible polymeric material is preferably the same as the substrate material. In addition, a method of permanently modifying the surface of a substrate material comprises subjecting the substrate surface to radio frequency plasma sufficient to raise the temperature at the substrate material to just above the glass transition temperature ($T_g$) of the substrate material for a time sufficient to produce a microscopically smooth, biocompatible surface on the substrate material. Further, a prosthesis used in mammals, including an intraocular lens, comprises a polymeric material core and a biocompatible polymeric material covalently grafted to the polymer core by radio frequency plasma induction.

6 Claims, No Drawings

BIOCOMPATIBLE, SURFACE MODIFIED MATERIALS

CROSS REFERENCE TO RELATED APPLICATIONS

This application is a division of U.S. patent application Ser. No. 07/820,169, filed Jan. 13, 1992, now U.S. Pat. No. 5,260,093, which was a continuation-in-part of U.S. patent application Ser. No. 07/342,270, filed Apr. 24, 1989, now issued as U.S. Pat. No. 5,080,924.

FIELD OF THE INVENTION

The present invention relates to methods of permanently modifying the surface of materials by plasma-induced and, where desired, post-plasma reactions to produce biocompatible, surface modified materials. In addition, the present invention relates to biocompatible, surface modified prostheses and, in particular, to a biocompatible, surface modified intraocular lens used in mammals.

BACKGROUND OF THE INVENTION

Prosthetic devices or prostheses are commonly used in medical procedures replacing or augmenting defective organs in mammals and humans, in particular, and are numerous and diverse in structure and application. Examples of prostheses include artificial joints, valve replacements, skin grafts, vascular grafts, shunts, plates and contact and intraocular lenses. Typically, prosthetic devices comprise natural and/or synthetic materials which are abrasive on the cellular level. Various prostheses in current use or in experimental use comprise metals, ceramics, silicone rubbers, polyesters, polyurethanes and/or polysulfones. Synthetic polymers, such as polymethylmethacrylate (PMMA) and hydroxyethylmethacrylate (HEMA), for example, are preferred polymers for prosthetic use in general and contact lenses and intraocular lenses in particular.

PMMA, for example, has several beneficial characteristics for such prosthetic use, including excellent light transmission, good optical clarity, resistance to fluid diffusion and in vivo deterioration, ease in processing (injection molding or machining, for example) and ease in implantation, such as an intraocular lens, an artificial joint and other implantable prostheses.

Typical lens prostheses, for example, are manufactured by machining, which leaves circular lathe marks or grooves visible at even relatively low magnification. These machining remnants render the lens unusable until the surface is smoothed, typically by a mechanical polishing process. However, the conventional polishing process generally takes several days to complete, has a failure rate in excess of 30% and fails to produce a microscopically smooth surface.

Abrasive prostheses, especially those which are implanted, can cause tissue irritation, edema and scarring. For example, posterior lens capsule opacification is a prevalent problem among those patients who have received intraocular lens implants comprising conventionally polished PMMA and other similar materials.

It is desirable to modify the surface properties of such abrasive materials without changing the beneficial characteristics thereof by developing a smooth surface thereby discouraging tissue adhesion and inhibiting cellular growth. Prostheses which do not promote tissue adhesion and do not inhibit cellular growth and which are not otherwise toxic to living systems may be considered "biocompatible." Surface modification to develop a biocompatible surface should be resistant to deterioration over time and should have no adverse effects on tissues and cells with which the surface modified material comes in contact.

Those skilled in the art have long recognized the need for biocompatible, surface modified materials for use in prosthetic devices and other materials. For example, U.S. Pat. No. 3,961,379 discloses a bioimplantable device manufactured from a cross-linked, swollen, hydrophilic polymer. These modified polymers must be solid and must be swellable by fluid swelling substances. Once swollen, the solid polymer is polymerized with a modifying substance by, for example, high energy particle radiation.

U.S. Pat. No. 4,189,364 discloses hydrophilic polymers formed in situ by irradiating a mixture of hydroxyalkyl methacrylate and a cross-linking agent. This patent discloses a process for forming hydrophilic polymer articles or hydrophilic polymer coatings on other substrates, such as glass or plastic, by polymerizing a hydrophilic monomer system by high energy particulate irradiation, such as accelerated electrons or nuclear particles including neutrons, protons, alpha, beta and/or gamma particles.

Radiation-induced grafting of acrylic acid onto other polymer films is disclosed by Gazard, M. et al., "Lithographic Technique Using Radiation-Induced Grafting of Acrylic Acid Into Poly(Methyl Methacrylate) Films," *Polymer Engineering and Science*, 20:16 (1980). Gazard et al. disclose that, under ionizing radiation, polymers undergo changes in their properties, especially in their solubility. Ionizing radiation of polymers leads to the formation of free radicals and other intermediates, which may be used to initiate the grafting of a monomer to produce a grafted copolymer with properties different from those of the initial polymer. For example, irradiated PMMA, onto which acrylic acid is grafted produces a graft copolymer which is insoluble in the solvents of PMMA.

U.S. Pat. No. 2,999,056 also discloses that an unsaturated organic acid may be attached to a shaped polymeric structure by ionizing radiation.

Other methods of altering the surface of polymeric objects include exposing the surface of a polymeric article to low temperature plasma or an electrically charged gaseous atmosphere, followed by contacting the surface of the polymeric article with a surface modifying compound as described, for example, in U.S. Pat. No. 4,344,981. This two-step method is generally called plasma-induced coating. Plasma induction has been described generally in U.S. Pat. No. 4,328,257, Yasuda, "Plasma for Modification of Polymers," *J. Macromol. Sci. C. Chem.*, 10(3):383 (1978), Mittal, "Interfacial Chemistry and Adhesion: Recent Developments and Prospects," *Pure & Appl. Chem*, 52:1295 (1980), Akovali, G. and Hasirci, N., "Polymerization of Hexamethyldisiloxane by Plasma on Activated Charcoal: Investigation of Parameters," *J. Appl. Polymer Sci.*, 29:2617 (1984) and Liu, W. T. et al., "Polymethyl Methacrylate Resist Sensitivity Enhancement in X-Ray Lithography by In Situ Polymerization," *Appl. Phys. Lett.*, 44:973 (1984), for example.

Ionized vapor or plasma discharge is typically created in a vacuum chamber in which the object to be modified is placed. The plasma discharge conditions the surface by creating free radicals and/or ions. It is known, for example, that exposing the surface of an object to plasma discharge, such as an oxygen plasma, enhances the wettability or hydrophilicity of such a surface. However, such treatment is only temporary. U.S. Pat. Nos. 3,925,178; 3,944,709; 4,072,769; 4,096,315; 4,122,942; 4,123,308; 4,131,691; 4,137, 365; 4,214,014 and 4,478,873 disclose examples of polymers whose surface characteristics have been modified by a plasma discharge.

Plasma discharge treatment may also be used to prepare an object for the attachment or grafting of a compound or material to the plasma discharge treated object. For example, a plasma discharge step may be used to condition the surface for grafting by creating free radicals to which a compound or material may be grafted. Such compounds or materials are generally called surface modifiers. Knight, P. M. et al., in "Surface Modification of Intraocular Lenses to Reduce Corneal Endothelial Damage," *Am. Intra-ocular Implants Soc. J.*, 5:123 (1979) disclose one example of a polymer object having a surface modifier attached thereto using gamma irradiation and radio frequency (RF) gas plasma treatment to generate free radicals on the surface of a PMMA intraocular lens followed by polymerizing hydrophilic monomers, in particular, HEMA and vinyl pyrrolidone, as a coating on the surface of the lens. While the coated surfaces exhibited enhanced hydrophilicity, the coated surfaces were not stable when boiled to sterilize them. Surface modification by gamma radiation followed by polymerization on the surface, on the other hand, remained intact through several hours of boiling. However, such coated PMMA surfaces were damaging to rabbit endothelial cells and surfaces coated with dissolvable coatings, such as polyvinyl acetate, were preferred.

Another example of a surface treated polymer is disclosed in U.S. Pat. No. 4,312,575. This patent discloses a soft, highly oxygen permeable, hydrophobic polymeric lens which has on its surface an ultra-thin, optically clear, permeable barrier coating which is the reaction product resulting from a glow discharge polymerization process conducted in a hydrocarbon or halogenated hydrocarbon gaseous atmosphere. While the plasma discharge process, itself, results in a hydrophilic surface, subsequent exposure to a glow discharge atmosphere of oxygen or ambient oxygen yields a still more hydrophilic surface.

U.S. Pat. No. 4,409,258 discloses a method for rendering contact lenses hydrophilic by bombarding the lens, which may be PMMA or silicone, with a positive ion beam generated by a plasma discharge, such as an oxygen plasma. The lens is thereafter hydrated, preferably at an elevated temperature.

Examples of surface treated polymeric lenses for use in humans are included in U.S. Pat. No. 3,880,818. This patent discloses a soft contact lens that is flexible and physiologically compatible, which is made by manufacturing a hard, inflexible prepolymer, such as a hard acrylic acid-type polymer, and reacting the inflexible prepolymer with an alcohol to esterify pendant carboxyl groups with alkyl groups, hydroxy alkyl groups or alkoxyalkyl groups, containing no more than eleven carbon atoms.

U.S. Pat. No. 4,143,949 discloses a discharge polymerization and coating process for making a hydrophilic contact lens from an oxygen permeable, hydrophobic polymer. The hydrophobic lens is placed in a glow discharge apparatus containing an atmosphere comprising a polymerizable organic monomer, such as hydroxyalkyl acrylate or methacrylate, glycidyl methacrylate, propylene oxide or N-vinyl-2-pyrrolidone, where the glow discharge is used to polymerize the monomer onto the surface of the contact lens.

Other examples of surface treated polymeric objects include U.S. Pat. Nos. 3,228,741; 3,925,178; 3,959,105; 3,985,697; 4,055,378; 4,277,595; 4,405,773; 4,430,458; 4,463,148; and 4,731,080. U.S. Pat. No. 4,731,080, for example, discloses a coated intraocular lens having a hydrophobic cross-linked vinyl-containing silicone polymer placed on the lens surface in solution.

It would be desirable to have a biocompatible, surface modified material and a method for producing the same, where the surface modification is substantially permanent, results in a smooth surface on the cellular level and where the surface modified material may be used, inter alia, as a prosthetic device in mammals. One such method is disclosed in U.S. Pat. No. 5,080,914, filed Apr. 24, 1989, the disclosure of which is incorporated herein by reference.

BRIEF SUMMARY OF THE INVENTION

According to the present invention, a method of permanently modifying the surface of a polymeric substrate material so that the substrate material develops a microscopically smooth, biocompatible surface comprises covalently grafting a biocompatible polymeric material to the surface of the substrate material by radio frequency plasma-induced grafting where the biocompatible polymeric material comprises substantially the same material as the material forming the substrate.

In addition, the present invention is directed to a method of permanently modifying the surface of a substrate material so that the substrate material develops a microscopically smooth, biocompatible surface comprising subjecting the substrate surface to radio frequency plasma sufficient to etch the substrate surface and raise the temperature at the surface to a temperature just above the glass transition temperature ($T_g$) of the substrate material.

Further, the present invention is directed to a prosthesis used in mammals comprising a polymer substrate or core and a biocompatible polymeric material grafted to the polymer core by plasma induction, the biocompatible polymer material comprising substantially the same material as the material forming the substrate.

DETAILED DESCRIPTION OF PREFERRED EMBODIMENTS

Although the methods of preparation of the invention apply generally to the preparation of permanent surface modification of many different materials, the methods are described and exemplified below with specific examples using polymeric intraocular lenses as prostheses which may be used in mammals. It will be understood by one skilled in the art that the methods of the present invention may be used to prepare permanently modified surfaces of other substrate materials, such as those prosthestic materials identified above. Moreover, it will be apparent to one skilled in the art that the methods of the present invention readily lend themselves to the preparation of materials having modified or enhanced surface characteristics having other uses.

According to one embodiment of the present invention, a biocompatible polymeric material is covalently grafted to the surface of a substrate material by radio frequency plasma induction. Examples of substrate materials to which a biocompatible material may be grafted include polymers, such as silicone, polypropylene, polyester, polytetrafluoroethylene, polyethylene terephthalate, polyurethane, PMMA, polyacrylic acid, or polymers of HEMA, ethylenediamine, diethylenetriamine, allylamine, hexamethyl-disiloxane, silazane and N-vinyl pyrrolidone.

Generally, the substrate material used in accordance with the present invention is chosen dependent upon its intended use. For example, PMMA and HEMA are two materials of choice for use in prosthetic devices intended for implantation or other application in mammals. However, in view of the present specification, one skilled in the art will appreciate that any organic polymer may be used as a substrate material, as well as certain ceramics and metals. Where an optically clear polymer for use in prosthetic devices for mammals is the substrate material, it is presently preferred that the polymer comprises PMMA.

The surface of the substrate material is modified by grafting a biocompatible polymeric material to the surface thereof. In some cases where it is desired to have only one material present, the first biocompatible polymeric material is substantially the same as the material forming the substrate. Once the substrate material surface has been modified by covalently grafting the biocompatible material to the surface of the substrate material, the modified surface should have properties which are relatively nontoxic and nonirritating to living tissues. In addition, the modified surface should not adversely affect the desired properties of the remainder of the substrate material, such as structural integrity and optical clarity, among others. In addition, the modified surface should be microscopically smooth. As used herein, the term "microscopically smooth" shall mean that the surface of the modified substrate should be featureless upon examination at an enlargement of about 3,000 to about 10,000×. In addition, where desired and depending on the properties of the first biocompatible polymeric material, the modified surface should be absent crystallinity, cross-linked and thermally stable.

Where the substrate material is intended for use in or as a prosthetic device, such as an intraocular lens, the surface modification of the present invention should not adversely affect the transparency or ocular acuity of the substrate material. Further, the first biocompatible material to be grafted to the substrate surface preferably comprises a material that is relatively easy to polymerize in a gas plasma environment. Such materials include unsaturated compounds or those compounds containing nitrogen, silicone or halogen. Materials that are relatively difficult to polymerize in a gas plasma environment include saturated compounds, cyclic compounds, compounds with a high molecular weight, such as proteins, and those compounds containing oxygen.

Examples of presently preferred biocompatible polymeric material include polyacrylic acid, silicone, polypropylene, polyester, polytetrafluoroethylene, polyethylene terephthalate, polyurethane, polymethylmethacrylate or polymers of ethylenediamine, diethylenetriamine, allylamine or hydroxyethylmethacrylate.

The biocompatible polymeric material should be grafted to the substrate material in a relatively uniform thickness and texture along the surface of the substrate material. In addition, especially where it is desired to use the substrate material as a prosthetic lens, it is preferred that the biocompatible polymeric material is present on the surface of the substrate material in a relatively small thickness to prevent interference with the optical clarity of the lens. More preferably, the biocompatible polymeric material is present in a monomolecular layer. In one embodiment of the present invention, for example, a surface modified substrate comprises a biocompatible polymeric material grafted to the surface of a substrate material with a biocompatible polymeric material thickness of about 100 A.

Grafting of the biocompatible polymeric material according to the present invention is conducted using radio frequency plasma-induced grafting. Other methods of grafting, such as electronic or ultra-violet (UV) radiation are not suitable where it is desired (as it is here) to modify only the surface of the substrate material. For example, where a prosthetic lens, such as a contact lens or intraocular lens, is desired to be modified, modification should be confined to the surface of the lens to avoid affecting the optical properties of the lens. Radio frequency plasma-induced grafting according to the present invention avoids structural modification below the outer-most surface layer, and generally results in more desirable optical properties.

Such gas plasma-induced grafting may be conducted in a radio frequency gas plasma reactor capable of generating a frequency of about 1 MHz to about 40 MHz. The frequency generated by a typical commercial gas plasma reactor is about 13.56 MHz, although one skilled in the art will recognize that higher and lower frequencies may be used to graft the biocompatible polymeric material to the surface of the substrate material in a radio frequency gas plasma reactor, depending on the substrate material and biocompatible polymeric material used, the relative ease or difficulty in preparing the surface of the substrate material for grafting, the relative ease or difficulty of vaporizing or polymerizing the biocompatible material, among other factors.

The first step of radio frequency plasma treatment according to this invention is the removal or etching of material from the surface of the substrate material being bombarded by the plasma. This process cleans the substrate and produces active species on the surface so treated, such as ions and free radicals, which can be used for inducing a graft reaction.

Generally, the rate of material removal may be controlled relative to the rate of deposition of a graft polymer by the frequency of the gas plasma, the power of the gas plasma, the treatment time, the gas used in the plasma, the gas pressure/concentration, and the type of bond desired on the treated substrate material surface, depending on the particular substrate material.

Plasma-induced grafting of the biocompatible polymeric material to the substrate material may be conducted in radio frequency plasma reactors known in the art. The Branson model 3003-1813 is one example of a suitable radio frequency gas plasma reactor which may be used to create a suitable gas plasma atmosphere in which a first biocompatible material having the properties described above may be vaporized and polymerized for grafting. One skilled in the art will appreciate, however, that other plasma reactors and apparatus may be used in accordance with the present invention.

Preferably, the ambient gas used in the radio frequency gas plasma-induced grafting is selected from the group consisting of nitrogen, ammonia and argon and other noble gases. More preferably, the gas used in the radio frequency gas plasma reaction is argon. Argon is an inert gas which creates active sites but does not produce new bonding when applied to a substrate surface in a RF gas plasma reactor. Oxygen, on the other hand, for example, tends to produce peroxides in such plasma-induced grafting reactions and is, therefore, generally less desired. Where no biocompatible material is to be grafted to the substrate surface (discussed below) or where the presence of reactive gas molecules on the substrate surface is not desired, it is presently preferred to use noble gas as ambient gas in the radio frequency gas plasma reactor, such as argon. One skilled in the art will be readily able to determine in view of this disclosure which suitable gases may be used in the plasma reaction in accordance with the present invention.

Surface modification by plasma-induced grafting in accordance with one embodiment of the present invention essentially comprises two steps: (1) plasma treatment or preparation of the substrate surface; and (2) introduction of the monomer of the biocompatible polymeric material into the plasma where the monomer becomes grafted to the substrate surface. As discussed above, the plasma treatment of the substrate surface breaks surface bonds, generating ions and free radicals at the surface of the substrate material, thus "activating" the surface. Introduction of the monomer into the radio frequency induced plasma causes the monomer to react with the substrate surface, polymerize and become grafted to the substrate surface.

The length of time the biocompatible material in an induced plasma state should be allowed to react with the substrate material depends upon several factors, including the plasma or radiation power, the radio frequency, the flow concentration or pressure, the temperature and the desired thickness of the grafted material. Preferably, the radiation power is about 10 watts to about 200 watts, depending upon the biocompatible material. For example, where the biocompatible material comprises silazane, hexamethyldisiloxane, PMMA, NVP or PAA, it is presently preferred that the radiation power is about 50 watts. Where the biocompatible layer material comprises HEMA (discussed below), it is presently preferred that the radiation power is about 10 watts to about 100 watts. In any event, except where desired, the reactor power used and the duration such power is used should be low and/or short enough so as to not induce thermal circulation and melt the substrate material. For example, where the substrate material comprises PMMA, the reaction conditions (i.e., power and duration) should not increase the temperature of the substrate material above about 40°–45° C. One skilled in the art may readily determine, in view of the plasma reaction variables described above, the desired plasma radiation power to be used in accordance with the present invention.

The plasma reaction is preferably conducted for a period of time of about 1 minute to about 60 minutes. More preferably, the plasma reaction is allowed to occur for a period of time of about 15 minutes to about 30 minutes. The flow concentration or vapor pressure of the plasma reactants in the reactor chamber should be low enough so that the particular monomer of the biocompatible material vaporizes when introduced into the reactor. Preferably, the vapor pressure is about 0.1 torr to about 0.6 torr. More preferably, the vapor pressure is about 0.4 torr.

The temperature in the plasma reaction should not be allowed to approach those temperatures which may damage the substrate material or the biocompatible material. High radiation power and any polymerization reaction (i.e., polymerization which may occur when the grafting reaction occurs; e.g.: polymerization to polymethylmethacrylate) tend to increase the temperature of the plasma reaction. It is desirable, therefore, to maintain the temperature in the plasma reaction below the temperature at which the substrate material and/or the graft material will be damaged, typically below about 40°–50° C.

In another embodiment of the present invention where no biocompatible material is grafted to the substrate, a microscopically smooth surface is obtained by plasma treatment of the substrate surface sufficient to etch the substrate surface and raise the temperature at the substrate surface to a temperature just above the glass transition temperature ($T_g$) of the substrate material. While not wishing to be bound by any particular theory, the inventors believe that, plasma treatment to induce an increase in temperature causes a thermal annealing at the surface of the substrate whereby irregular surface features (such as surface peaks, etc.) relax, evening out such irregularities. Where temperatures above the glass transition temperature are desired, relatively higher radiation power is preferred. For example, to reach a surface temperature of about 105° C., which is the glass transition temperature of PMMA, radiation power of about 100 to about 120 watts is preferred. One skilled in the art may readily determine glass transition temperature by reference to publicly available materials characteristics tables and determine the temperature obtainable at a given wattage in a given reactor factoring in time, efficiency of the reaction chamber and the surface area of the substrate, for example. The radiation power used and the time the substrate is exposed to such radiation should be such to avoid thermal circulation of the substrate beneath the surface and melting of the substrate.

In view of this disclosure, one skilled in the art may readily determine the reactants, time, pressure and temperature conditions for a reaction using given materials without undue experimentation. For example, in one embodiment of the present invention, methyl methacrylate liquid is introduced into a plasma reactor chamber having a plasma-etched or treated body of PMMA where, because of the low pressure within the chamber, the methyl methacrylate vaporizes. The methyl methacrylate is exposed to about 50 to about 150 watts of radio frequency radiation at about 27.5° C. at a reactant or vapor pressure of about 0.4 to about 0.5 Torr.

Novel products having a permanently modified surface resulting from the method of the present invention include prostheses, such as an intraocular lens, for use in mammals having a permanently modified, biocompatible surface, which comprises a polymer lens body and a biocompatible, polymeric material grafted thereto, where the biocompatible, polymeric material comprises substantially the same material as the material forming the polymer lens body, such as PMMA.

In addition, novel products produced using the method of the present invention include prostheses for use in mammals comprising a polymeric material substrate having a permanently modified surface where the surface was modified by subjecting the substrate surface to radio frequency plasma sufficient to raise the temperature at the substrate surface to just above the glass transition temperature.

The invention will now be illustrated in further detail by reference to the following specific, non-limiting examples.

EXAMPLE I

An intraocular lens manufactured by CILCO from PMMA was abraded using 1 micron aluminum oxide particles to produce grooves on the surface of the lens of 1 micron depth. Macroscopically, the lens had a hazy appearance. The lens was cleaned in a 1% sodium dodecyl sulfate (SDS) solution and then thoroughly rinsed in deionized water to remove any contaminants that may be present from the manufacturing process or subsequent handling. The lens was positioned in a Branson 3000 Series radio frequency plasma reactor in a glass treatment fixture. The pressure inside the reactor was reduced to less than about 0.1 Torr for approximately 10 minutes. Argon gas (Ar) was then introduced at approximately 8 psi and the pressure inside the reactor was adjusted to 0.5 Torr for 10 minutes to purge the chamber with the argon gas. Radio frequency power was then turned on to 120 watts while maintaining chamber pressure at 0.5 Torr. Treatment with the argon gas plasma continued for approximately 60 minutes. After this time, radio frequency power was turned off and the chamber was purged to normal atmospheric pressure to open the chamber door. Macroscopically, the lens appeared clean and clear. Upon microscopic examination, some surface irregularities or memory of the initial grooves was apparent.

EXAMPLE II

An intraocular lens was treated using the procedures of Example I. After turning off the radio frequency power, the chamber was then pumped down to a pressure of 0.1 Torr for approximately 5 minutes to evacuate the chamber. Methylmethacrylate (MMA) monomer was then introduced into the reactor chamber at maximum flow rate (approximately 0.8 Torr) and radio frequency power was turned on to 70 watts for 30 minutes. After this time, MMA delivery was discontinued and the radio frequency power was shut down. The chamber was then purged to normal atmospheric pressure to open the chamber door. Macroscopically and microscopically, the lens was free of any surface irregularities, surpassing the surface quality of the original, commerical lens.

The present invention may be embodied in other specific forms without departing from the spirit or essential attributes thereof and, accordingly, reference should be made to the appended claims, rather than the specification, as indicating the scope of the invention.

We claim:

1. A prosthesis for use in mammals comprising a polymeric substrate material having a permanently modified microscopically smooth, biocompatible surface thereon, produced by covalently grafting a polymeric biocompatible material to the surface of the substrate material by radio frequency plasma induction, the biocompatible polymeric material comprising substantially the same material as the polymeric substrate and being physically grafted by covalent bonds to the substrate material, and the modified microscopically smooth, biocompatible surface being substantially free of surface irregularities at a magnification of at least 3,000×.

2. The prosthesis according to claim 1, wherein the biocompatible polymeric material is selected from the group consisting of polyacrylic acid, silicone, polypropylene, polyester, polytetrafluoroethylene, polyethylene terephthalate, polyurethane, polymethylmethacrylate and polymers of ethylenediamine, diethylenetriamine, allylamine or hydroxyethylmethacrylate.

3. A prosthesis used in mammals having a permanently modified, microscopically smooth, biocompatible surface comprising:

(a) a polymeric material core; and (b) a biocompatible polymeric material covalently grafted to the surface of the polymeric material core by radio frequency plasma induction, the biocompatible polymeric material comprising substantially the same material as the core.

4. The prosthesis according to claim 3, wherein the polymeric material is selected from the group consisting of polyacrylic acid, silicone, polypropylene, polyester, polytetrafluoroethylene, polyethylene terephthalate, polyurethane, polymethylmethacrylate, and polymers of ethylenediamine, diethylenetriamine, allylamine or hydroxyethylmethacrylate.

5. An intraocular lens having a permanently modified, smooth, biocompatible surface, comprising a polymeric material lens body, and a biocompatible polymeric material, said biocompatible polymeric material being covalently grafted to the surface of the lens body by radio frequency plasma induction and comprising substantially the same material as the body.

6. The intraocular lens according to claim 5, wherein the biocompatible polymeric material is selected from the group consisting of polyacrylic acid, silicone, polypropylene, polyester, polytetrafluoroethylene, polyethylene terephthalate, polyurethane, polymethylmethacrylate and polymers of ethylenediamine, diethylenetriamine, allylamine or hydroxyethylmethacrylate.

* * * * *